United States Patent
Yoshimura et al.

(10) Patent No.: US 8,367,368 B2
(45) Date of Patent: Feb. 5, 2013

(54) D-SERINE DEHYDRATASE AND USE THEREOF

(75) Inventors: Tohru Yoshimura, Nagoya (JP); Tomokazu Ito, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 13/430,583

(22) Filed: Mar. 26, 2012

(65) Prior Publication Data

US 2012/0244520 A1    Sep. 27, 2012

Related U.S. Application Data

(62) Division of application No. 12/445,642, filed as application No. PCT/JP2007/070193 on Oct. 16, 2007, now abandoned.

(30) Foreign Application Priority Data

Oct. 18, 2006 (JP) ................................ 2006-283398

(51) Int. Cl.
| | |
|---|---|
| *C12Q 1/26* | (2006.01) |
| *C12N 9/00* | (2006.01) |
| *C12N 9/02* | (2006.01) |
| *C12N 1/20* | (2006.01) |
| *C12N 15/00* | (2006.01) |
| *C07H 21/04* | (2006.01) |

(52) U.S. Cl. ....... 435/25; 435/183; 435/189; 435/252.3; 435/320.1; 536/23.2

(58) Field of Classification Search .................. None
See application file for complete search history.

(56) References Cited

U.S. PATENT DOCUMENTS

2006/0166300 A1    7/2006 Esaki et al.

OTHER PUBLICATIONS

Lesson, P.D. et al., "The Glycine Site on the NMDA Receptor: Structure-Activity Relationships and Therapeutic Potential," J. Med. Chem. 37, 1994, pp. 4053-4067.
Hashimoto K., et al., "Decreased Serum Levels of D-Serine in Patients With Schizophrenia," Arch. Gen. Psychiatry 60, 2003, pp. 572-576.
Hashimoto K., et al., "Reduced D-serine to total serine ratio in the cerebrospinal fluid of drug native schizophrenic patients," Prog Neuro-psychopharmacology Biol Psychiatry 29, 2005, pp. 767-769.
Hashimoto K., et al., "Possible role of D-serine in the pathophysiology of Alzheimer's disease," Prog Neuro-psychopharmacology Biol Psychiatry 28, 2004, pp. 385-388.
Hamase, K., "Sensitive Determination of D-Amino Acids in Mammals and the Effect of D-Amino-Acid Oxidase Activity on Their Amounts," Biological & Pharmaceutical Bulletin, 2005, 28, pp. 1578-1584.
Federiuk C.S. et al., "Characterization of the catalytic pathway for D-serine dehydratase," Evidence for variation of the rate-determining step with substrate structure. J Biol Chem., 258(9), 1983, pp. 5379-5385.
Kikuchi, S. et al., "A D-Serine dehydratase acting also on L-serine from *Klebsiella pneumonias*," J Biochem., 84(5), 1978, pp. 1133-1138.
Database GenBank, Accession No. NC-001139 REGION:129888.. 131174 (2 pages).
M. Larsson et al., "High-throughput protein expression of cDNA products as a tool in functional genomics," J Biotechnol 80(2), 2000, pp. 143-157.
K. Misawa et al., "A method to identify cDNAs based on localization of green fluorescent protein fusion products," Proc. Natl. Acad. Sci. U.S.A. 97(7), 2000, pp. 3062-3066.
T. Sawsaki et al., "A cell-free protein synthesis system for high-throughput proteomics," Proc. Natl. Acad. Sci. U.S.A. 99 (23), 2002, pp. 14652-14657.
International Search Report mailed on Jan. 15, 2008, issued on PCT/JP2007/070193.
Ito, T. et al.,"Enzymatic assay of D-serine using D-serine dehydratase from *Saccharomyces cerevisiae*," Analytical Biochemistry, vol. 371, No. 2, 2007, pp. 167-172.
Marceau, M et al., "D-Serine Dehydratase From *Escherichia-coli*, DNA Sequence and Identification of Catalytically Inactive Glycine to Aspartic Acid Variants," Journal of Biological Chemistry, vol. 263, No. 32, 1988, pp. 16926-16933.
Blandin, G., et al., "Genomic exploration of the hemiascomycetous yeasts: 4. The genome of *Saccharomyces cerevisiae* revisited," FEBS Letters vol. 487, No. 1, 2000, pp. 31-36.
Supplemental European Search Report dated Dec. 8, 2009, issued on the corresponding European Patent Application No. 07 82 9927.
Chica et al., Curr Opin Biotechnology. Aug. 2005, 16(4) pp. 378-384.
Sen et al., Appl Biochem Ciotechnology, Dec. 2007 143(3) pp. 212-223.
Accession P53095. Publichsed Oct. 1, 1996.

*Primary Examiner* — Christian Fronda
(74) *Attorney, Agent, or Firm* — Edwards Wildman Palmer LLP; James E. Armstrong, IV; Elbert Chiang

(57) ABSTRACT

A novel D-serine quantification method that can overcome various disadvantages of a conventional D-serine quantification method; a novel enzyme that can be used in the D-serine quantification method; a gene encoding the enzyme; and the like. Specifically, a novel D-serine dehydratase including (a) a protein having an amino acid sequence set forth in SEQ ID NO: 1 or (b) a protein having an amino acid sequence homologous to the amino acid sequence set forth in SEQ ID NO: 1 and having a D-serine dehydratase activity; and a D-serine quantification method including the steps of reacting a sample with the enzyme, quantifying ammonia or pyruvic acid produced by the reaction, and calculating the amount of D-serine in the sample based on a value produced by the quantification.

6 Claims, 9 Drawing Sheets

Fig.1

```
            10         20         30         40         50         60
       MSDVLSQYKG CSVRDLPTPN FVINEEKFDK NCTTMLNNVE KLSQECGVPI KFRAHVKTHK
            70         80         90        100        110        120
       TAKGTLKQLG HGLPLAKRTT RAILVSTLKE AEELLNYQDR QCSDYIDDIT YSLPCCVPEF
           130        140        150        160        170        180
       IPLLSNLSRR VNNFQVFVDN IEHLENLKNF GRPASGKKWS VFIKVDMGTK RAGLAFDSPE
           190        200        210        220        230        240
       FLSLLKKLTS SEIKEVIEPY GFYAHAGHSY SSTSINDTQN LLMEEVKAVN SAAKVLCSVD
           250        260        270        280        290        300
       PQFDPSKLTL SVGATPTSNS LKLDNKSTLV KFITTQLVST LEIHCGNYCM YDLQQVATGC
           310        320        330        340        350        360
       VQDHELSGFV LGTVLSSYPS RGELLSNTGV MCLTREASSI KGFGICADLE HVLKSESFSR
           370        380        390        400        410        420
       EWYVARVSQE HGILRPIRNW NETTPLKLGS KIAVLPQHAC ITMGQFPYYF VVNSEGIVND

VWLPFQKW
```

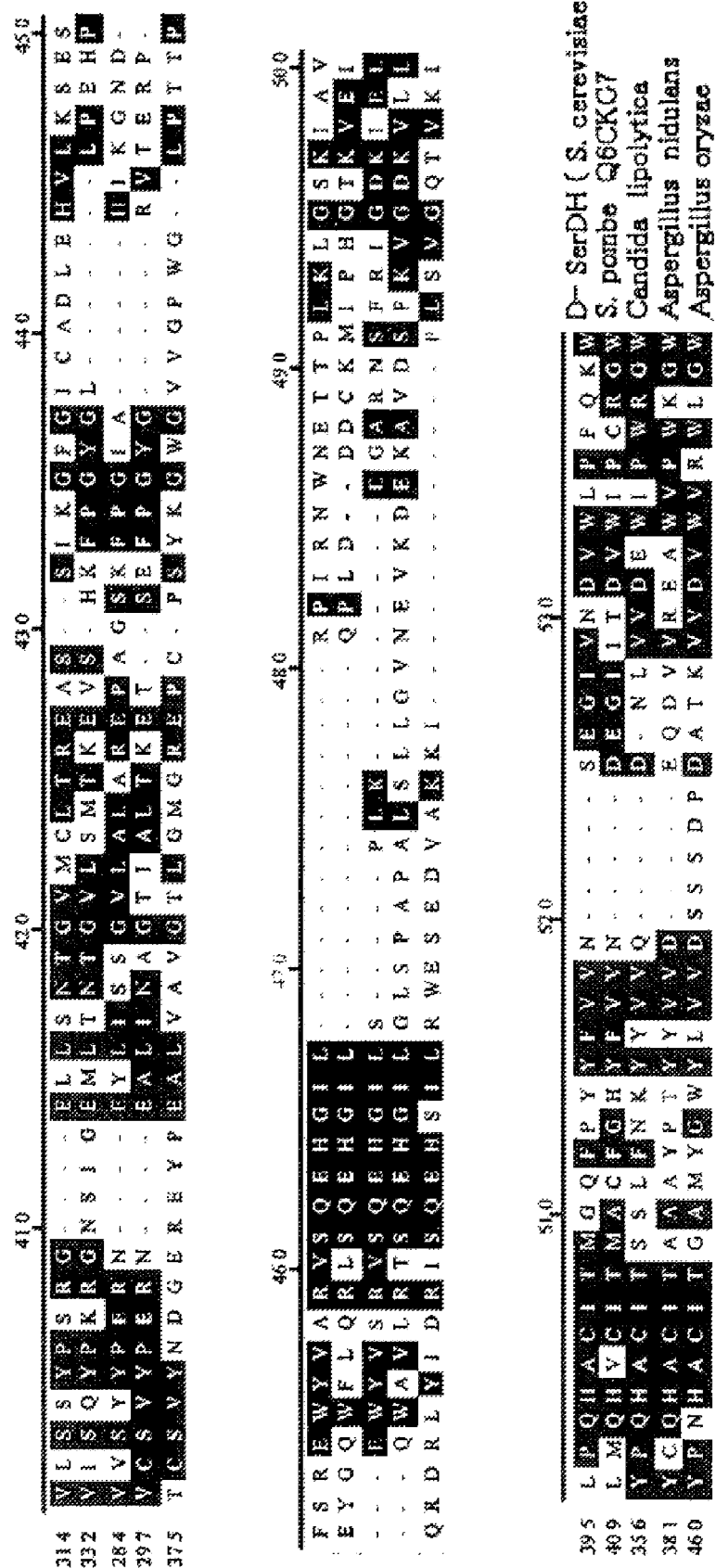

|  | yeast D-SerDH | E. coli D-SerDH |
|---|---|---|
| D-Ser | 100 | 100 |
| L-Ser | n.d. | 0.0013 |
| D-Thr | 3.7 | 16.7 | measured by Nessler method
n.d. : not detected $V_{max}$ = 4.2 µmol / min mg    $K_m$ = 0.46 mM

| method | D-Ser concentration (µM) | |
| --- | --- | --- |
| enzyme method | 243±7.0 | (n = 6) |
| HPLC method | 239±9.8 | (n = 6) |

D-SERINE DEHYDRATASE AND USE THEREOF

CROSS-REFERENCE TO RELATED APPLICATION(S)

This application is a divisional of U.S. patent application Ser. No. 12/445,642, filed on Apr. 15, 2009, which is the U.S. national phase, pursuant to 35 U.S.C. §371, of international application No. PCT/JP2007/070193, filed on Oct. 16, 2007, which claims priority to Japanese Application No. 2006-283398, filed on Oct. 18, 2006.

TECHNICAL FIELD

The present invention relates to D-serine dehydratase. More particularly, the present invention relates to D-serine dehydratase derived from eukaryote and use thereof.

BACKGROUND ART

Amino acid has L- and D-enantiomers. L-amino acid is known to play an important role in forming a protein and to exhibit various bioactivities in a living body. On the other hand, although D-amino acid has been known to be constituents of a cell wall and be essential for bacteria to grow, the role of D-amino acid in eukaryotes has not been clarified. Recently, it has been known that D-amino acid has an important physiological function also in eukaryotes. Among D-amino acids, as to D-serine, there have been some reports: D-serine exists in the mammalian brain in a liberation state and acts as a coagonist of an NMDA receptor (non-patent document 1); in the cerebral spinal fluid or the serum of patients with schizophrenic disorder, the D-serine content is significantly reduced and the ratio of the D-serine content in the total serine content (D-serine content/total serine content) is also significantly reduced (non-patent documents 2 and 3); and the ratio of the D-serine content in the total serine content (D-serine content/total serine content) is also significantly reduced in the serum of patients with Alzheimer's disease (non-patent document 4), etc. In particular, much attention has been paid on the relationship with respect to nervous diseases. Although the application of D-serine in the future is being expected in this way, no simple quantification method exists in the current state. A quantification method of D-serine by using an enzyme has not been established. The quantification of serine has exclusively been carried out by a quantification method by HPLC or capillary electrophoresis after labeling with a fluorescence reagent, and the like, or a quantification method of serine by using gas chromatography (GC) after derivatization (non-patent document 5).

[Non-patent document 1] Lesson, P. D., and Iverson, L. L. (1994) J. Med. Chem. 37, 4053-4067.
[Non-patent document 2] Hashimoto et al. (2003) Arch. Gen. Psychiatry 60, 572
[Non-patent document 3] Hashimoto et al. (2005) Prog Neuropsychopharmacol Biol Psychiatry 29, 767
[Non-patent document 4] Hashimoto et al. (2004) Prog Neuropsychopharmacol Biol Psychiatry. 28, 385-8.
[Non-patent document 5] Sensitive Determination of D-Amino Acids in Mammals and the Effect of D-Amino-Acid Oxidase Activity on Their Amounts. Biological & Pharmaceutical Bulletin. (2005), 28, 1578
[Non-patent document 6] Characterization of the catalytic pathway for D-serine dehydratase. Evidence for variation of the rate-determining step with substrate structure. J Biol Chem. (1983) 258(9): 5379-5385.
[Non-patent document 7] D-serine dehydratase acting also on L-serine from *Klebsiella pneumoniae*. J Biochem. 1978 November; 84 (5): 1133-1138.

DISCLOSURE OF THE INVENTION

Problems to be Solved by the Invention

A current D-serine quantification method has some problems, for example, it requires skills, it takes a lot of time, it requires expensive instruments such as HPLC and capillary electrophoresis and GC, it is difficult to secure the safety in clinical application because it is difficult to be disposed of. That is to say, the current method needs complicated pre-treatment such as derivatization by using an unstable fluorescence reagent. In addition, when a living body sample such as blood and spinal fluid is analyzed, the noise of L-amino acid, which exists in a larger amount than D-serine, makes it difficult to analyze the results. Consequently, in this state, only persons with high skill can carry out accurate quantification. Furthermore, in a standard analysis using HPLC, it takes about 30 minutes per specimen excluding pre-treatment time. The use of expensive analyzing instrument makes it difficult to analyze a large number of specimens simultaneously and a person who analyzes the specimen has to use the same instrument repeatedly, so that infection risk to the person is increased. In order to overcome the above-mentioned various problems, a quantification method of D-serine using an enzyme has been desired. D-serine dehydratase of bacteria (*Escherichia coli*, *Klebsiella pneumoniae*) that is a currently available enzyme reacts with L-serine although it is only a little (non-patent documents 6 and 7). In general, since the amount of L-serine in the living body sample is much larger than that of D-serine, the reactivity with respect to L-serine makes it difficult to apply the enzyme derived from such bacteria to the quantification of D-serine.

It is therefore an object of the present invention to provide a novel D-serine quantification method that can overcome various disadvantages of a conventional D-serine quantification method. It is another object of the present invention to provide a novel enzyme used for the D-serine quantification method, and a gene encoding the enzyme; and the like.

Means to Solve the Problem

Under the above-mentioned circumstances, the present inventors have keenly investigated and resulted in finding a novel D-serine dehydratase derived from *Saccharomyces cerevisiae*. When the structural characteristic of this enzyme was examined, it has been shown that this enzyme breaks D-serine down to pyruvic acid and ammonia the same as in the already-known bacteria-derived D-serine dehydratases (D-serine deaminase and D-serine ammonia-lyase (EC4.3.1.18)) but that this enzyme does not have a homology to the already-known D-serine dehydratase in the primary structure. Furthermore, surprisingly, this enzyme does not react with L-serine at all, and it is therefore determined that this enzyme has an extremely high substrate-specificity. This property means that this enzyme is extremely useful in the quantification of D-serine. With this enzyme, it is possible to accurately quantify the amount of D-serine in a sample, and it is possible to quantify D-serine, in a living body sample, which has much larger content of L-serine than the content of D-serine under the conditions in which quantification cannot be carried out with a conventional enzyme.

The present invention is based on the above-mentioned results and findings, and provides the below-mentioned D-serine dehydratase, and a gene encoding the enzyme, as well as a quantification method of D-serine.

[1] D-serine dehydratase comprising the following protein (a) or (b):
   (a) a protein having an amino acid sequence set forth in SEQ ID NO: 1; or
   (b) a protein having an amino acid sequence homologous to the amino acid sequence set forth in SEQ ID NO: 1 and having a D-serine dehydratase activity.
[2] The D-serine dehydratase according to [1], which does not react with L-serine.
[3] The D-serine dehydratase according to [1] or [2], wherein a reactivity to D-threonine is not more than 5% when a reactivity to D-serine is 100%.
[4] The D-serine dehydratase according to any of [1] to [3], which is a recombinant protein expressed in *Escherichia coli* as a host.
[5] A D-serine dehydratase gene comprising any of DNA selected from the group consisting of the following (A) to (C):
   (A) DNA encoding an amino acid sequence set forth in SEQ ID NO: 1;
   (B) DNA having a base sequence set forth in SEQ ID NO: 2; and
   (C) DNA having a base sequence homologous to the base sequence set forth in SEQ ID NO: 2 and encoding a protein having a D-serine dehydratase activity.
[6] A vector for expressing D-serine dehydratase, including a gene according to [5].
[7] A transformant into which a gene according to [5] is introduced.
[8] A production method for D-serine dehydratase, the method including the steps of:
   (1) culturing the transformant according to [7] in a condition in which a protein encoded by the gene is produced; and
   (2) collecting the produced protein.
[9] A reagent for quantifying D-serine including the D-serine dehydratase according to any of [1] to [4].
[10] A kit for quantifying D-serine including the reagent for quantifying D-serine according to [9] and an instruction.
[11] A D-serine quantification method including the following steps of:
   (1) preparing a reagent;
   (2) adding D-serine dehydratase according to any of claims 1 to 4 into the sample and reacting with each other;
   (3) quantifying ammonia or pyruvic acid generated as a result of (2); and
   (4) calculating an amount of D-serine in the sample from the quantified value obtained in (3).
[12] The D-serine quantification method according to [11], the method further including the following steps of:
   (5) adding amino acid racemase to a reaction solution after the step (2) and reacting with each other in a coexistence of the D-serine dehydratase;
   (6) quantifying ammonia or pyruvic acid generated as a result of (5); and
   (7) calculating a total amount of serine in the sample from the quantified value obtained in (6) and the amount of D-serine calculated in (4).
[13] A D-serine quantification method including the following steps of:
   (1) preparing a sample:
   (2) adding the D-serine dehydratase according to any of [1] to [4] to a part of the sample so as to react with each other;
   (3) quantifying ammonia or pyruvic acid generated as a result of (2); and
   (4) calculating an amount of serine in the sample from the quantified value obtained in (3);
   (5) adding the D-serine dehydratase and amino acid racemase described in any of [1] to [4] to another part of the sample and reacting with each other;
   (6) quantifying ammonia or pyruvic acid generated as a result of (5); and
   (7) calculating a total amount of serine in the sample from the quantified value obtained in (6).

BRIEF DESCRIPTION OF THE DRAWINGS

FIG. 1 shows an amino acid sequence of a novel D-serine dehydratase derived from *Saccharomyces cerevisiae* (SEQ ID NO: 1).

FIG. 3 shows a comparison of amino acid sequences between the novel D-serine dehydratase and a protein (YGL196W homologue) that is homologous in the primary structure to the enzyme. The homology between the novel D-serine dehydratase and YGL196W homologue from various origins is 38.3% (*S. pombe*), 26.3% (*A. nidulans*), 29.1% (*C. lipolytica*), and 17.1% (*A. oryzae*), respectively. The functions of YGL196W homologues obtained from the result of search are not known.

BEST MODE OF CARRYING OUT THE INVENTION

Terms

Figure 2:
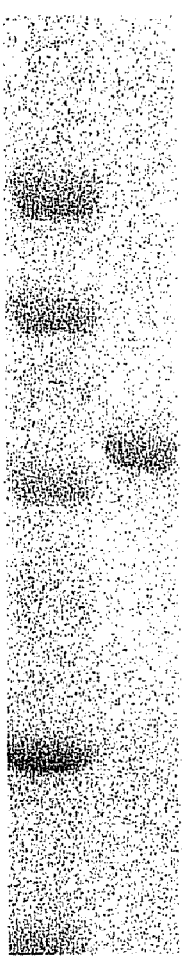
FIG. 2 shows a result of SDS-PAGE of the novel D-serine dehydratase. Left lane shows a molecular weight marker, and right lane shows a sample lane. An apparent molecular weight of a novel D-serine dehydratase is about 50 kDa.

In the present invention, "DNA encoding a protein" refers to DNA from which a protein is obtained when the DNA is expressed, that is to say, it refers to DNA having a base sequence corresponding to an amino acid sequence of the protein. Therefore, degeneracy of codon is also considered.

In the specification, the term "disease" is used interchangeably with disorder, illness, pathologic condition, or the like, showing a not-normal state.

As used herein, the terms "isolated" and "purified" are used interchangeably. The term "isolated" used about D-serine dehydratase of the present invention refers to a state in which, when the enzyme of the present invention is derived from a natural material, any components other than the enzyme are not substantially included in a natural material (in particular, a contaminated protein is not substantially included). Specifically, in the isolated enzyme of the present invention, the content of the contaminated protein on a weight basis is, for example, less than about 20%, preferably less than about 10%, further preferably less than about 5%, and still further preferably, less than about 1% with respect to the total weight. On the other hand, when the enzyme of the present invention is prepared by a genetically engineering technique, the term "isolated" refers to a state that is free from other components derived from the used host cell, a culture medium, or the like. Specifically, in the isolated enzyme of the present invention, the content of the contaminated components on a weight basis is, for example, less than about 20%, preferably less than about 10%, further preferably less than about 5%, and still further preferably, less than about 1%, with respect to the total weight. Unless otherwise specified clearly, in the present invention, merely described "D-serine dehydratase" means "isolated D-serine dehydratase." The same is true in the term "enzyme" used instead of D-serine dehydratase.

The term "isolated" used about DNA refers to a state in which, when DNA originally exists in a native state, the DNA is separated from other nucleic acid co-existing in a native state. However, the DNA may include a part of other nucleic acid components such as a nucleic acid sequence flanking in the native state (for example, a sequence of a promoter region or a terminator sequence). For example, when the DNA is a genome DNA, preferably, the "isolated" state does not substantially include other DNA components co-existing in a native state. On the other hand, when the DNA is a cDNA molecule and the like which is prepared by a genetically engineering technique, preferably, the "isolated" state does not substantially include cell components, culture solution, and the like. Similarly, when the DNA is a chemically synthesized DNA, preferably, the "isolated" state does not include a precursor (raw material) such as dDNTP, chemical materials used in the synthesis process, and the like. Unless otherwise specified clearly, in the present invention, merely described "DNA" means "isolated DNA."

In this specification, the term "include (comprise) . . . " or "including (comprising) . . . " is used to include the meaning of "consisting of . . . ."

(D-Serine Dehydratase)

A first aspect of the present invention provides a novel D-serine dehydratase based on the finding that a gene with unknown function of *Saccharomyces cerevisiae* encodes D-serine dehydratase. Hereinafter, for the convenience of description, the D-serine dehydratase of the present invention is also referred to as an "enzyme of the present invention."

In one embodiment, the enzyme of the present invention includes a protein having an amino acid sequence set forth in SEQ ID NO: 1. The amino acid sequence is registered in Genebank (http://www.ncbi.nlm.nih.gov/Genbank/index.html) as an amino acid sequence encoding a protein with unknown function (Accession: P53095, DEFINITION: Uncharacterized protein YGL196W).

An enzyme of the present invention breaks down D-serine to pyruvic acid and ammonia similar to the already-known bacteria-derived D-serine dehydratases (D-serine deaminase and D-serine ammonia-lyase (EC4.3.1.18)), but the enzyme of the present invention does not have a homology to the already-known D-serine dehydratase in a primary structure.

As shown in the below-mentioned Example, the enzyme has an extremely high substrate-specificity to D-serine. That is to say, the enzyme is not observed to have a reactivity with respect to L-serine and it has extremely low reactivity with respect to D-threonine (the reactivity to D-threonine was 5% when the reactivity to D-serine was 100%). Thus, the enzyme of the present invention is excellent in the substrate-specificity as compared with the already-known enzyme of the same kind.

In general, when a part of the amino acid sequence of a certain protein is modified, the modified protein may sometimes have a protein before modification. That is to say, the modification of the amino acid sequence does not have a substantial effect on the function of the protein, so that the function of the protein may be often maintained before and after the modification. Thus, as another exemplary embodiment, the present invention provides a protein having an amino acid sequence homologous to the amino acid sequence set forth in SEQ ID NO: 1 and the D-serine dehydratase activity (hereinafter, which is referred to as "homologous protein"). The "homologous amino acid sequence" herein denotes an amino acid sequence that is partly different from the amino acid sequence set forth in SEQ ID NO: 1 but this difference does not have a substantial effect on the function (herein, the D-serine dehydratase activity) of the protein.

The "partial difference in the amino acid sequence" typically denotes that mutation (change) occurs in an amino acid sequence due to deletion or substitution of one to several amino acids constituting the amino acid sequence, or addition or insertion of one to several amino acids constituting the amino acid sequence, or the combination thereof. The difference in the amino acid sequence is permitted as long as the D-serine dehydratase activity is maintained (more or less change in the activity is permitted). As long as this condition is satisfied, the position in which a difference in the amino acid sequence occurs is not particularly limited and the difference may occur in a plurality of positions. The plurality herein signifies a numerical value corresponding to less than about 30%, preferably less than about 20%, further preferably less than about 10%, still further preferably less than about 5%, and most preferably less than about 1% with respect to the total amino acid. That is to say, the homologous protein has, for example, about 70% or more, preferably about 80% or more, further preferably about 90% or more, still further preferably about 95% or more and most preferably about 99% or more of similarly to the amino acid sequence set forth in SEQ ID NO: 1.

Preferably, a homologous protein is obtained by allowing conservative amino acid substitution to be generated in an amino acid residue that is not essential to the D-serine dehydratase activity. Herein, "conservative amino acid substitution" denotes a substitution of an amino acid residue to an amino acid residue having a side chain of the same property. The amino acid residue is classified into some families according to its side chain, for example, the basic side chain (for example, lysin, arginine, histidine), the acid side chain (for example, asparatic acid, glutamic acid), the uncharged polar side chain (for example, glycine, asparagine, glutamine, serine, threonine, tyrosine, cysteine), the nonpolar side chain (for example, alanine, valine, leucine, isleucine, proline, phenyl alanine, methionine, tryptophane), β branched side chain (for example, threonine, valine, isleucine), and the aromatic side chain (for example, tyrosine, phenyl alanine, tryptophane, histidine). The conservative amino acid substitution is carried out between the amino acid residues in the same family.

Herein, the identity (%) between two amino acid sequences or two nucleic acids (hereinafter, referred to as "two sequences" as a term including the both) can be determined by the following procedure. Firstly, two sequences are aligned for optimum comparison of the two sequences (for example, a gap may be introduced into the first sequence so as to obtain an optimum alignment with respect to the second sequence). When a molecule (amino acid residue or nucleotide) at the specific position in the first sequence and a molecule in the corresponding position in the second sequence are the same, the molecules in the positions are defined as being identical. The identity between two sequences is a function of the number of identical positions shared by the sequences (i.e., identity (%)=number of identical positions/total number of positions×100), in which the number of gap and the length of each gap, which were required for optimization of alignment of the two sequences are preferably considered.

The comparison and determination of identity between two sequences can be carried out by using a mathematical algorithm. A specific example of mathematical algorithm that can be used for comparing sequences include an algorithm described in Karlin and Altschul (1990) Proc. Natl. Acad. Sci. USA 87:2264-68 and modified by Karlin and Altschul (1993) Proc. Natl. Acad. Sci. USA 90:5873-77 but the algorithm is not necessarily limited to this. Such an algorithm is incorporated in NBLAST and XBLAST programs (version 2.0) of Altschul et al. (1990) J. Mol. Biol. 215: 403-10. In order to obtain a nucleotide sequence homologous to the nucleic acid molecule of the present invention, for example, BLAST nucleotide search with score=100 and wordlength=12 may be carried out in NBLAST program. BLAST polypeptide searches may be carried out by, for example, the NBLAST program, score=50, wordlength=3 to obtain amino acid sequence homologous to the polypeptide molecule of the present invention. In order to obtain gapped alignments for the purpose of comparison, Gapped BLAST as described in Altschul et al., (1997) Amino Acids Research 25(17): 3389-3402 can be utilized. When utilizing BLAST and Gapped BLAST programs, the default parameters of the respective programs (e.g., XBLAST and NBLAST) can be used. In detail, see http://www.ncbi.nlm.nih.gov. Another example of mathematical algorithm that can be used for comparing sequences includes an algorithm of Meyers and Miller (Comput. Appl. Biosci. 4: 11-17 (1988)) which has been incorporated into the ALIGN program that can be used for, for example, GENESTREAM network server (IGH Montpellier, France) or ISREC server. When the ALIGN program is used for comparison of the amino acid sequences, for example, a PAM120 weight residue table can be used with a gap length penalty of 12 and a gap penalty of 4.

The identity between two amino acid sequences can be determined using the GAP program in the GCG software package, using a Blossom 62 matrix or PAM250 matrix and a gap weight of 12, 10, 8, 6, or 4, and a gap length weight of 2, 3, or 4. Furthermore, the homology between two nucleic acid sequences can be determined using the GAP program in the GCG software package (available at http://www.gcg.com) with a gap weight of 50 and a gap length weight of 3.

The enzyme of the present invention can be prepared easily by a genetic engineering technique. For example, an appropriate host cell (for example, *Escherichia coli*) is transformed by DNA encoding the protein of the present invention, and recovering proteins expressed in the transformant. The recovered proteins are appropriately purified according to the purposes. In the case where the enzyme of the present invention is prepared as a recombinant protein, various modifications can be carried out. For example, DNA encoding the enzyme of the present invention and other appropriate DNA are inserted into the same vector and the vector is used for producing a recombinant protein. Then, the enzyme including a recombinant protein in which other peptide or protein is linked to can be obtained. Furthermore, modification such as addition of sugar chain and/or lipid or processing of N-terminus or C-terminus may be carried out. The above-mentioned modification permits extraction of a recombinant protein, simplification of purification, addition of biological functions, or the like.

Note here that a preparation method of the enzyme of the present invention is not limited to a method by a genetically engineering technique. For example, when an enzyme exists in nature, the enzyme of the present invention can be prepared from a natural material by a standard technique (pulverizing, extraction, purification, and the like). Note here that the enzyme of the present invention can be prepared in an isolated state in general.

Note here that no intron exists and, therefore, the sequence of cDNA corresponds to the sequence of a genome DNA.
(DNA encoding D-serine dehydratase)

A second aspect of the present invention provides a gene encoding the enzyme of the present invention, that is, a novel D-serine dehydratase gene.

In one exemplary embodiment, the gene of the present invention includes DNA encoding the amino acid sequence set forth in SEQ ID NO: 1. Specific examples of this exemplary embodiment include DNA consisting of the base sequence set forth in SEQ ID NO: 2 and DNA consisting of the base sequence set forth in SEQ ID NO: 3. The base sequence set forth in SEQ ID NO: 2 is full-length cDNA of protein YGL196W. Note here that no intron exists and, therefore, the sequence of cDNA corresponds to the sequence of a genome DNA.

In general, when a part of DNA encoding a certain protein is modified, a protein encoded by the modified DNA may sometimes have the equal function as a protein before modification. That is to say, the modification of the DNA sequence does not have a substantial effect on the function of the encoded protein, so that the function of the encoded protein is often maintained before and after the modification. Thus, as another exemplary embodiment, the present invention provides DNA having a base sequence homologous to the base sequence set forth in SEQ ID NO: 2 and encoding a protein having a D-serine dehydratase activity (hereinafter, which is referred to as "homologous DNA"). The "homologous DNA" herein denotes a base sequence that is partly different from the base sequence set forth in SEQ ID NO: 2 but that does not substantially affect the function of the protein encoded by the base sequence (herein, D-serine dehydratase activity) due to the difference.

A specific example of the homologous DNA includes DNA that hybridizes to the complementary base sequence of base sequence of SEQ ID NO.: 2 under stringent conditions. Herein, the "stringent conditions" are referred to as conditions in which a so-called specific hybrid can be formed and a nonspecific hybrid cannot be formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15M NaCl, 15 mM sodium citrate, pH 7.0), 5× Denhardt solution, 1% SDS, 10% dextran sulfate, and 10 μg/ml denatured salmon sperm DNA, 50 mM phosphate buffer (pH 7.5)) is used and incubated at about 42° C. to about 50° C., thereafter, 0.1×SSC and 0.1% SDS are used and washed at about 65° C. to about 70° C. Further preferable stringent conditions can include conditions in which, for example, as a hybridization solution, 50% formamide, 5×SSC (0.15M NaCl, 15 mM sodium citrate, pH 7.0), 1× Denhardt solution, 1% SDS, 10% dextran sulfate, 10 μg/ml denatured salmon sperm DNA and 50 mM phosphate buffer (pH 7.5) are used.

Another specific example of the homologous DNA can include DNA encoding a protein having a base sequence including substitution, deletion, insertion, addition or inversion in one or a plurality of bases when the base sequence of SEQ ID NO.: 2 is a reference base sequence, and having a D-serine dehydratase activity. The substitution, deletion, or the like, of the base may occur in a plurality of sites. The "plurality" herein denotes, for example, 2 to 40 base sequences, preferably 2 to 20 base sequences, and more preferably 2 to 10 base sequences, although it depends upon the positions or kinds of the amino acid residue in the three-dimensional structure of the protein encoded by the DNA. The above-mentioned homologous DNA can be obtained by modifying DNA having a base sequence of SEQ ID NO.: 2 so as to include substitution, deletion, insertion, addition and/or inversion of base by using a site specific mutation method by, for example, a treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York); random mutagenesis (Molecular Cloning, Third Edition, Chapter 13, Cold Spring Harbor Laboratory Press, New York), and the like. Furthermore, homologous DNA can be obtained by other method such as irradiation with ultraviolet ray.

A further example of the homologous DNA can include DNA having difference in base as mentioned above due to polymorphism represented by SNP.

The gene of the present invention can be prepared in an isolated state by standard genetic engineering technique, molecular biological technique, biochemical technique, and the like, with reference to sequence information disclosed in this specification or attached sequence list. Specifically, the gene of the present invention can be prepared by appropriately using oligonucleotide probe/primer capable of specifically hybridizing the gene of the present invention from appropriate genome DNA library or cDNA library of yeasts, or cell body extract of yeasts. An oligonucleotide primer can be easily synthesized by using, for example, a commercially available automated DNA synthesizer. As to a production method of libraries used for preparing the gene of the present invention, see, for example, Molecular Cloning, Third Edition, Cold Spring Harbor Laboratory Press, New York.

For example, a gene having a base sequence set forth in SEQ ID NO: 2 can be isolated by using a hybridization method using an entire or a part of the complimentary sequence as a probe. Furthermore, amplification and isolation can be carried out by using a nucleic acid amplification reaction (for example, PCR) using a synthesized oligonucleotide primer designed to specifically hybridize to a part of the base sequence.

(Vector)

Another aspect of the present invention relates to a vector containing the gene of the present invention. The term "vector" as used in this specification is intended to refer to a nucleic acid molecule capable of transporting another nucleic acid that is inserted into the vector to the inside of the target such as cells. The form of vector is not particularly limited and therefor examples of the vector may include a plasmid vector, a cosmid vector, a phage vector, a viral vector (e.g., an adenovirus vector, an adeno-associated virus vector, a retrovirus vector, a herpes virus vector).

According to the purpose of use (cloning, protein expression), and by considering the kinds of host cells, an appropriate vector is selected. Specific examples of a vector include a vector using *Escherichia coli* as a host (M13 phage or the modified body thereof, λ, phage or the modified body thereof, pBR322 or the modified body thereof (pB325, pAT153, pUC8, etc.) and the like), a vector using yeast as a host (pYepSec1, pMFa, pYES2, etc.), a vector using insect cells as a host (pAc, pVL, etc.), a vector using mammalian cells as a host (pCDM8, pMT2PC, etc.).

The vector of the present invention is preferably an expression vector. The term "expression vector" is a vector capable of introducing the nucleic acid inserted therein into the target cells (host cells) and expressing in the cells. The expression vector usually includes a promoter sequence necessary for expression of the inserted nucleic acid and an enhancer sequence for promoting the expression, and the like. An expression vector including a selection marker can be used. When such an expression vector is used, by using the selection marker, the presence or absence of the introduction of an expression vector (and the degree thereof) can be confirmed.

Insertion of the gene of the present invention, insertion of the selection marker gene (if necessary), and insertion of a promoter (if necessary), and the like, into a vector can be carried out by a standard recombination DNA technology (see, for example, Molecular Cloning, Third Edition, 1.84, Cold Spring Harbor Laboratory Press, New York, a already-known method using restriction enzyme and DNA ligase).

(Transformant)

The present invention further relates to a transformant into which the gene of the present invention is introduced. In the transformant of the preset invention, the gene of the present invention exists as an exogenous molecule. The transformant of the present invention can be preferably prepared by transfection or transformation using the vector of the present invention mentioned above. The transfection and the like can be carried out by, for example, a calcium phosphate coprecipitation method, electroporation (Potter, H. et al., Proc. Natl. Acad. Sci. U.S.A. 81, 7161-7165(1984)), lipofection (Felgner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73,366-370 (1976)), and the like.

Examples of the host cell may include bacterial cell (for example, *Escherichia coil*), yeast cell (for example, *Saccharomyces cerevisiae, Schizosaccharomyces pombe, Pichia pastoris*), and the like.

(Production Method of D-Serine Dehydratase)

By using the above-mentioned transformant, D-serine dehydratase can be produced. Then, a further aspect of the present invention provides a production method of D-serine dehydratase by using the above-mentioned transformant. In the production method of the present invention, a step of culturing the above-mentioned transformant is carried out in a condition in which a protein encoded by a gene introduced therein is produced. As to various vector-host systems, the culture conditions for transformant are well-known (see, for example, Oshima et al., Post-Sequence Protein Experimentation 2, "Preparation Method of Sample" Tokyo Kagaku Dojin Co., Ltd., 2002). A person skilled in the art can set appropriate culture conditions easily.

After culturing, a step of recovering the produced protein (that is to say, D-serine dehydratase) is carried out. The intended protein can be recovered from a culture solution or a cell body. When the protein is produced outside the cell body, the protein is recovered from the culture solution, and in other case, the protein can be recovered from inside the cell body. When the protein is recovered from the culture solution, the intended protein can be obtained by separation and purification after removing insoluble matters by, for example, filtration, centrifugation of culture supernatant followed by carrying out any combinations of salting out of ammonium sulfate precipitation, dialysis, various types of chromatographies, and the like. On the other hand, when the intended protein is recovered from a cell body, the intended protein can be obtained by pulverizing the cell body by pressuring treatment, ultrasonication, and the like, followed by separation and purification thereof similar to the above. Note here that after the cell body may be recovered from a culture solution by filtration, centrifugation, and the like, followed by carrying out the above-mentioned series of processes (pulverizing, separation, and purification of cell body).

(Application of D-Serine Dehydratase)

The present invention further provides an application of the enzyme of the present invention. Although some D-serine dehydratases (enzyme of *Escherichia coli* described in non-patent document 6, enzyme of *Klebsiella pneumoniae* described in non-patent document 7, and the like) have been found, quantification of D-serine using D-serine dehydratase has not been reported. This is anticipated because the substrate-specificity of the already-known enzyme is low. The enzyme of the present invention is excellent in the substrate-specificity as compared with the same kinds of already-known enzymes and does not substantially have the reactivity with respect to L-serine. With the enzyme of the present invention having such properties, it is possible to selectively quantify D-serine in a sample. Thus, the enzyme of the present invention is suitable for quantification of D-serine. That is to say, the enzyme of the present invention is useful as a reagent for quantifying D-serine. Therefore, the present invention provides a reagent for quantifying D-serine including the enzyme of the present invention.

The present invention further provides a quantification method of D-serine using the enzyme of the present invention (hereinafter, which is referred to as "the quantification method of the present invention"). The D-serine quantification method of the present invention is based on the following principle. That is to say, D-serine in a sample is broken down by using the enzyme of the present invention having a high specificity with respect to D-serine, and the generated ammonia or pyruvic acid is quantified.

The quantification method of the present invention includes the following steps of: (1) preparing a sample; (2) adding D-serine dehydratase of the present invention to the sample and reacting with each other; (3) quantifying ammonia or pyruvic acid generated as a result of the step (2); and (4) calculating the amount of the D-serine in the sample from the quantified value obtained in the step (3). These steps are carried out sequentially in this order. Hereinafter, each step is described in detail.

1. Step (1)

In this step, a sample is prepared. Kinds of the sample are not particularly limited and examples of the sample may include samples (for example, blood, serum, lymph, spinal fluid, bone marrow, tissue extract, plant extract, cell extract, and the like) derived from a living body (human or non-human animals and plants, and microorganisms) or samples (for example, food, drugs, livestock food, soil, river and ocean water, and the like) derived from a non-living body. These samples may be prepared by routine procedures.

2. Step (2)

In this step, the D-serine dehydratase of the present invention is added to a sample and reacted with each other. The addition amount of the D-serine dehydratase is set to, for example, 1 μg/ml to 50 μg/ml but it is not necessarily limited to thereto. The reaction temperature is set to, for example, 20° C. to 40° C., and preferably, 30° C. to 37° C. The pH of the reaction solution is set in the range from about 7.5 to about 9.0, preferably around pH 8. The pH can be adjusted by using Tris buffer solution or HEPES buffer solution. The reaction time is set to, for example, 5 minutes to 3 hours. The measurement over time may be carried out.

The above-mentioned reaction conditions are described as one example, and therefore a part of all of them can be appropriately modified. A person skilled in the art can modify or optimize a reaction condition through the preliminary experiment.

It is preferable that this step is carried in the presence of pyridoxal-5'-phosphate. That is to say, it is preferable that pyridoxal-5'-phosphate together with D-serine dehydratase is added to a sample. Since pyridoxal-5'-phosphate is originally covalently linked to D-serine dehydratase, it is not essential to add pyridoxal-5'-phosphate to a reaction system. However, with the addition of pyridoxal-5'-phosphate, even when pyridoxal-5'-phosphate is dropped in a part of an enzyme molecule, accurate and highly reliable experiment data can be obtained. The amount of pyridoxal-5'-phosphate to be added is, for example, 0.25 μg/ml to 5 μg/ml but it is not particularly limited thereto.

3. Step (3)

In this step, quantification of ammonia or pyruvic acid generated in the step (2) is carried out. For the quantification of ammonia, a Nessler method (see, for example, John, C et al., (1976) Biochemical J. 159: 803-806), an indophenol method (see, for example, J. Berthelot: Report chem Appt 1, 284, 1859, Japanese Patent Application Examined Publication No. S58-11024, Japanese Patent Application Unexamined Publication No. S61-38463, and Japanese Patent Application Unexamined Publication No. S61-44351), and an enzyme method of allowing glutamate dehydrogenase, NADPH and α-ketoglutarate to react with ammonia in blood plasma and measuring the change amount of the absorbance according to the reduction of NADPH (see, for example, Japanese Patent Application Unexamined Publication No. S50-23699), and the like can be used. Among them, it is preferable to use the Nessler method and the indophenol method because they can be carried out in a simple and easy procedure and they do not require special instrument and device.

On the other hand, the quantification method of pyruvic acid includes a method of coupling pyruvic acid and lactate dehydrogenase to each other and analyzing the decrease in the absorbance according to the oxidation of NADH in the region of ultraviolet ray (see, for example, Nishimura et al. (1991) Biochemistry 30, 4032-4077, edited by Japan Association of Clinical Research, "In vitro diagnostic agents," p 488, Yakuji Nippo, Ltd. (1991)), and a method for oxidizing pyruvic acid with oxygen and analyzing hydrogen peroxide generated according to the progress of the reaction, and the like. Note here that in addition to these methods, various quantification methods of pyruvic acid have been proposed (see, for example, Japanese Patent Application Unexamined Publications No. S62-14799, No. H4-346796, No. H5-95798, and No. H5-219991). Any of the methods can be used.

Among them, the method using lactate dehydrogenase and the method using pyruvate oxidase are preferable because they can be carried out by a simple and easy procedure and they do not require special instrument and device.

With two or more of the measurement methods, ammonia (or pyruvic acid) may be quantified. Thus, it is possible to verify the quantification value by each measurement method and the reliability of the quantification result can be improved. For the same purpose, both ammonia and pyruvic acid may be quantified.

4. Step (4)

In this step, from the quantified value of ammonia or pyruvic acid obtained in the step (3), the amount of D-serine in a sample is calculated. In general, by forming a calibration curve showing a relationship between the amount of ammonia or pyruvic acid and the amount of D-serine in advance by using a plurality of samples whose D-serine content has been determined, the quantified value of ammonia or pyruvic acid is compared with the calibration curve, thus calculating the amount of D-serine in a sample.

In one embodiment of the present invention, after the steps (1) to (4), the following steps are carried out: (5) adding amino acid racemase to a reaction solution after the step (2) and reacting with each other in the presence of the D-serine dehydratase; (6) quantifying ammonia or pyruvic acid generated as a result of the step (5); and (7) calculating the total amount of serine in the sample from the quantified value obtained in the step (6) and the amount of D-serine calculated in the step (4), sequentially in this order.

In the quantification method of this embodiment, the amount of D-serine in a sample is quantified, and meanwhile, by using amino acid racemase, L-serine in a sample is converted into D-serine, thereby quantifying the total amount of serine in the sample. That is to say, according to the quantification method in this embodiment, in addition to the amount of D-serine in a sample, the total amount of serine (that is to say, total of the amount of D-serine and the amount of L-serine) is calculated. Thus, the ratio of the amount of D-serine to the total amount of serine can be clarified.

According to a recent report, the ratio of the D-serine content in the total serine content (D-serine content/total serine content) is significantly reduced in the cerebral spinal fluid or the serum of patients with schizophrenic disorder, and in the serum of patients with Alzheimer's disease (non-patent documents 2 to 4). Thus, the quantification method in this embodiment provides information (data) useful for diagnosis of schizophrenic disorder and Alzheimer's disease. Furthermore, in diagnosis of not only schizophrenic disorder and Alzheimer's disease, but also diagnosis of various diseases that are recognized to have a relationship between the ratio of the D-serine content in the total serine content and the onset and progressing state or pathologic condition and the like, the quantification method of this embodiment is expected to be used.

Hereinafter, each characteristic step in this embodiment is described in detail.

5. Step (5)

In this step, amino acid racemase is added to a reaction solution after step (2) and reacted with each other. Since the previously added D-serine dehydratase and pyridoxal-5'-phosphate coexist in the reaction solution after the step (2), an enzyme reaction with amino acid racemase and an enzyme reaction with D-serine dehydratase proceed simultaneously.

Note here that in the quantification method of this embodiment, after the step (2), a part of the reaction solution is sampled and the sampled reaction solution is used to carry out the step (3), and the rest of the reaction solution (or a part thereof) is used in the step (5).

Any enzymes can be used as amino acid racemase of the present invention as long as they have an activity of converting L-serine into D-serine. Therefore, amino acid racemase used in the present invention is not limited to an enzyme that is generally regarded as serine racemase. However, in order to convert L-serine into D-serine efficiently, serine racemase is preferably employed. As the serine racemase, bacterial racemase (see, Toru Yoshimura (2005) Vitamin 79, 277-283) and animal racemase (see, Arias C. A. et al., (2000) Microbiology 146, 1727-1734) are known.

The addition amount of amino acid racemase is set to, for example, 1 µg/ml to 50 µg/ml but not necessarily limited to this amount. The reaction conditions (reaction temperature, reaction pH, and reaction time) of this step conform to the reaction conditions in the above-mentioned step (2) in principle. However, a part or all of the conditions may be appropriately modified. Furthermore, a person skilled in the art can modify and optimize the reaction conditions through the preliminary experiment.

When a sufficient effect of the previously added D-serine dehydratase is not expected, for example, when D-serine dehydratase may be deactivated, the amount of D-serine generated by the effect of amino acid racemase is excessive, or the like, D-serine dehydratase may be added together with amino acid racemase. Furthermore, it is preferable that this step is carried out in the presence of pyridoxal-5'-phosphate. In this stage, pyridoxal-5'-phosphate may be added.

6. Step (6)

In this step, ammonia or pyruvic acid generated as a result of the step (5) is quantified. That is to say, D-serine generated by the effect of amino acid racemase is broken down with D-serine dehydratase, thereby generating ammonia or pyruvic acid, and the amount of the generated ammonia or pyruvic acid is quantified. This step is carried out by the same method in the above-mentioned step (3).

7. Step (7)

In this step, a total amount of serine in the sample is calculated from the quantified value of ammonia or pyruvic acid obtained in the step (6) and the amount of D-serine calculated in the step (4). Firstly, by using the quantified value obtained in the step (6), the amount of L-serine that has originally existed in the sample is calculated. By adding the amount of D-serine (the amount of D-serine that has been originally existed in a sample) calculated in the step (4) to the resultant amount of L-serine, the total amount of seine is obtained. Note here that the amount of L-serine can be calculated by the same method as the calculation method of D-serine in the step (4), that is to say, the amount can be calculated by a method using a calibration curve showing the relationship between the amount of ammonia or pyruvic acid and the amount of D-serine.

In the above-mentioned embodiments, by using a sample (reaction solution) with which D-serine dehydratase is reacted, the reaction between D-serine dehydratase and amino acid racemase is further carried out so as to quantify the amount of L-serine in the sample. However, as mentioned below, the quantification of the amount of D-serine by D-serine dehydratase and the quantification of the amount of L-serine by D-serine dehydratase and amino acid racemase can be carried out independently. That is to say, another embodiment of the present invention provides a D-serine quantification method including the following steps of: (1)

preparing sample; (2) adding the D-serine dehydratase of the present invention to a part of the sample and reacting with each other; (3) quantifying ammonia or pyruvic acid generated as a result of the step (2); (4) calculating a total amount of serine in the sample from the quantified value obtained in the step (3); (5) adding the D-serine dehydratase and amino acid racemase to another part of the sample and reacting with each other; (6) quantifying ammonia or pyruvic acid generated as a result of the step (5); and (7) calculating a total amount of serine in the sample from the quantified value obtained in the step (6). Any of the steps (2) to (4) and the steps (5) to (7) may be carried out earlier and may be carried out concurrently.

The quantified value obtained in the step (6) reflects the amounts of L-serine and D-serine, which have been originally existed in a sample. Therefore, the total amount of serine in the sample can be calculated from the quantified value obtained in the step (6), (step (7)). Note here that each step in this embodiment can be carried out by the same method and the conditions of the above-mentioned corresponding steps.

The present invention further provides a kit for carrying out a quantification method of the present invention. According to the kit, the quantification method of the present invention can be carried in a simpler and easier way for a shorter time. The kit of the present invention includes D-serine dehydratase of the present invention (reagent for quantifying D-serine) as an essential component. Furthermore, one or more reagents (for example, buffer solution, pyridoxal-5'-phosphate, D-serine as a standard reagent), instruments, and the like, which are necessary to the detection of the reaction of the enzyme or the reaction product, may be included in a kit. It is preferable that a kit used for quantifying the total serine content may includes amino acid racemase in addition to D-serine content in a sample. Furthermore, it is furthermore preferable that a kit includes one or more reagents (for example, buffer solution, pyridoxal-5'-phosphate, D-serine as a standard reagent), instruments, and the like, which are necessary to the detection of the reaction of the enzyme or the reaction product. In general, a kit of the present invention is includes an instruction.

Note here that matters which the present specification does not refer to (conditions, operation methods, and the like) may follow the routine methods. See, for example, for example, Oshima et al., Post-Sequence Protein Experimentation 2, "Preparation Method of Sample" Tokyo Kagaku Dojin Co., Ltd., 2002).

EXAMPLE

1. Search of Novel D-Serine Dehydratase

Novel D-serine dehydratase is searched by the following method. By BLAST search, a gene, YGL196W, which is thought to encode protein having a three-dimensional structure homologous to the N-terminal domain of bacterial alanine racemase was found on a genome of *Saccharomyces cerevisiae*. Then, by the below-mentioned method, protein encoded by the gene, YGL196W, was prepared. By using the prepared protein, the production of ammonia was measured by the below-mentioned method by using D-serine, L-serine, D-threonine and L-threonine as a substrate. As a result, it is determined that a protein of *Saccharomyces cerevisiae*, YGL196W, with unknown functions (FIG. 1, SEQ ID NO: 1) has a D-serine dehydratase activity. Note here that a sequence of cDNA encoding the protein is shown in SEQ ID NO: 2.

2. Preparation and Analysis of Novel D-Serine Dehydratase
(1) Gene Cloning

PCR was carried out by using chromosome DNA of *Saccharomyces cerevisiae* BY4742 strain (the American Type Culture Collection (ATCC)) as a template and using the following primers.

```
                                         (SEQ ID NO: 3)
5'-atgctcgaggttctatctcaatataaagggtgctcag-3'

(SEQ ID NO: 4)
5'-accaagcttaccatttctgaaaaggtaaccaaacatcg-3'
```

The obtained DNA fragment was cleaved with XhoI and HindIII, and then ligated to pET15b (Novagen) which had been cleaved with the same restriction enzymes. Note here that the constructed plasmid pDsdSC encodes D-serine dehydratase to which an amino acid tag of total 16 residues including six His residues at N terminal and 10 residues including a thrombin cleavage site is added.

(2) Expression and Purification of Protein

According to a routine procedure, a plasmid pDsdSC was introduced into *Escherichia coil* BL21 (DE3) (Novagen). BL21 (DE3) cells after the introduction were planted on 5 ml of LB medium containing 50 μg/ml ampicillin and cultured at 37° C. over night. This was planted on 200 ml of the same medium and cultured at 37° C. When the turbidity of the culture solution measured at 610 nm became 0.5, IPTG (final concentration: 0.5 mM) was added and cultured at 30° C. for three hours. Cells were collected and washed, and then suspended in a binding buffer (20 mM Tris HCl (pH 7.9) containing 500 mM NaCl and 5 mM imidazole) and subjected to ultrasonic disintegration. The supernatant obtained by centrifugation at 20,000×g for 30 minutes was applied to a Ni-chelating column equilibrated with a binding buffer (Novagen His-Bind Resin). It was washed with a washing buffer having an amount of 10 times larger than that of the washing buffer (20 mM Tris HCl (pH 7.9) containing 500 mM NaCl and 80 mM) and eluted with an elution buffer (20 mM Tris HCl (pH 7.9) containing 500 mM NaCl and 1 M imidazole). An active fraction was dialyzed with 500 times amount of A buffer (20 mM Tris HCl (pH 7.5) containing 140 mM NaCl) and then applied to DEAE-TOYOPEARL column (10 ml) equilibrated with A buffer containing $2\times10^{-5}$ M pyridoxal-5'-phosphate. The purity of the enzyme eluted with this buffer was confirmed (FIG. 2).

(3) Measurement of Activity

D-serine dehydratase catalyzes a reaction expressed by the following reaction formula.

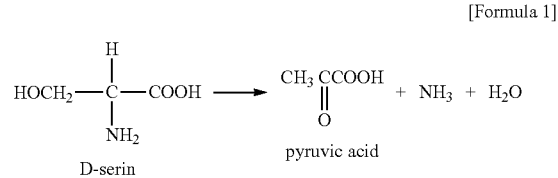

[Formula 1]

The activity of serine dehydratase was measured as follows: ammonia as a reaction product was measured by a Nessler method or pyruvic acid as a reaction product was measured by coupling with lactate dehydrogenase and by oxidation of NADH. Hereinafter, outline of each method is shown.

(a) Nessler Method

To a reaction solution (final volume: 200 μl) containing 50 mM of HEPES-NaOH buffer (pH 8.0), 20 μmol of pyridoxal-5'-phosphate and 10 mM of D-serine, an appropriate amount of D-serine dehydratase was added and incubated at 30° C. Thereafter, trichloroacetic acid (final concentration: 5%) was added to stop the reaction. Ammonia in the centrifuged supernatant was quantified by using a Nessler reagent.

(b) Method Using Lactate Dehydrogenase

To a reaction solution containing 50 mM of HEPES-NaOH buffer (pH 8.0), 20 μmol of pyridoxal-5'-phosphate, 10 mM of D-serine, 0.3 mM of NADH and 20 units of lactate dehydrogenase (final volume: 1 ml), an appropriate amount of D-serine dehydratase was added and reacted at 30° C. The decrease in absorbance at 340 nm accompanying the conversion from NADH to NAD was measured.

When the activity of the purified enzyme was measured by the Nessler method, the specific activity was 3.7 gmol/min/mg.

(4) Investigation of Primary Structure of Novel Enzyme

Figure 3:
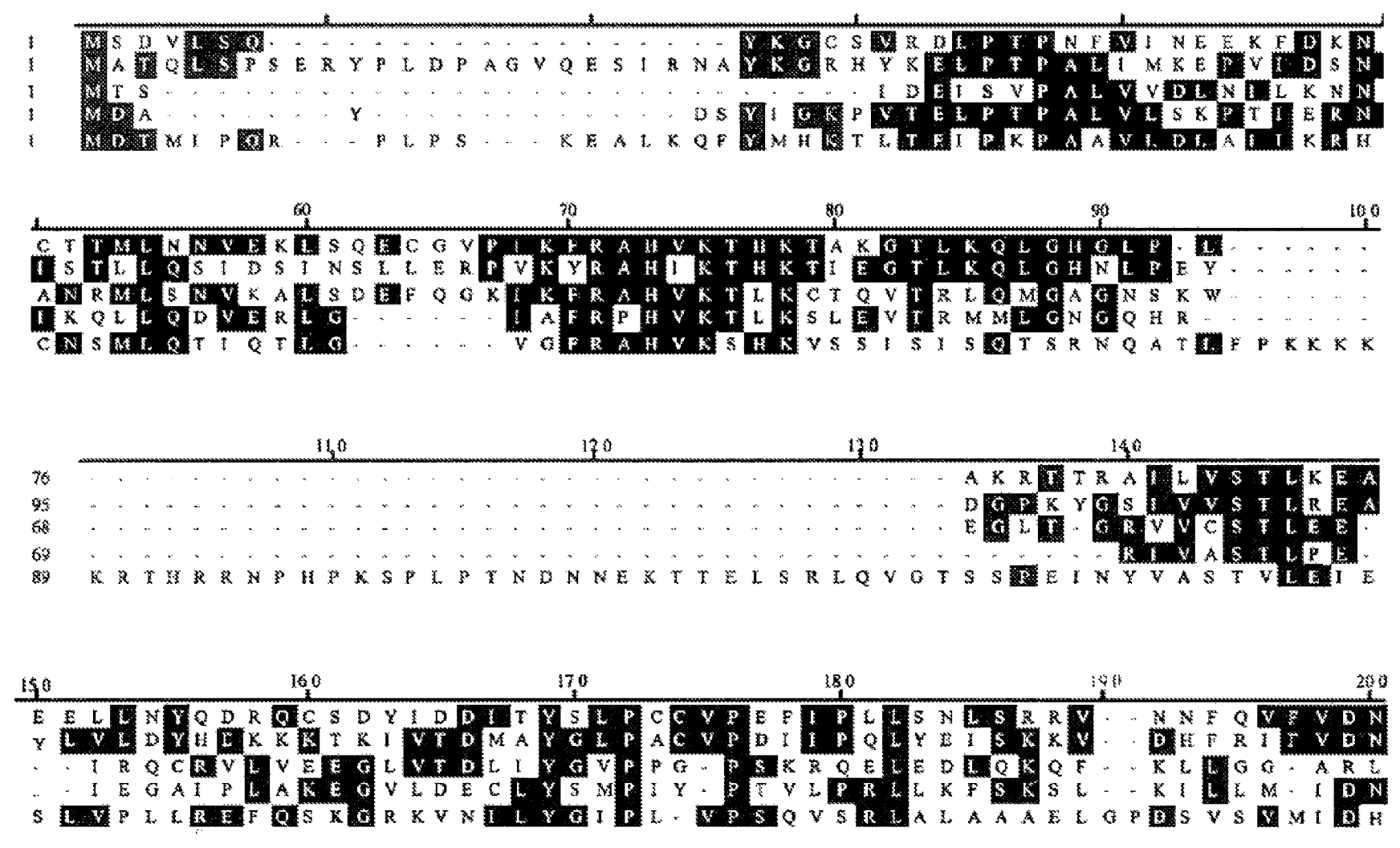
Figure 3:
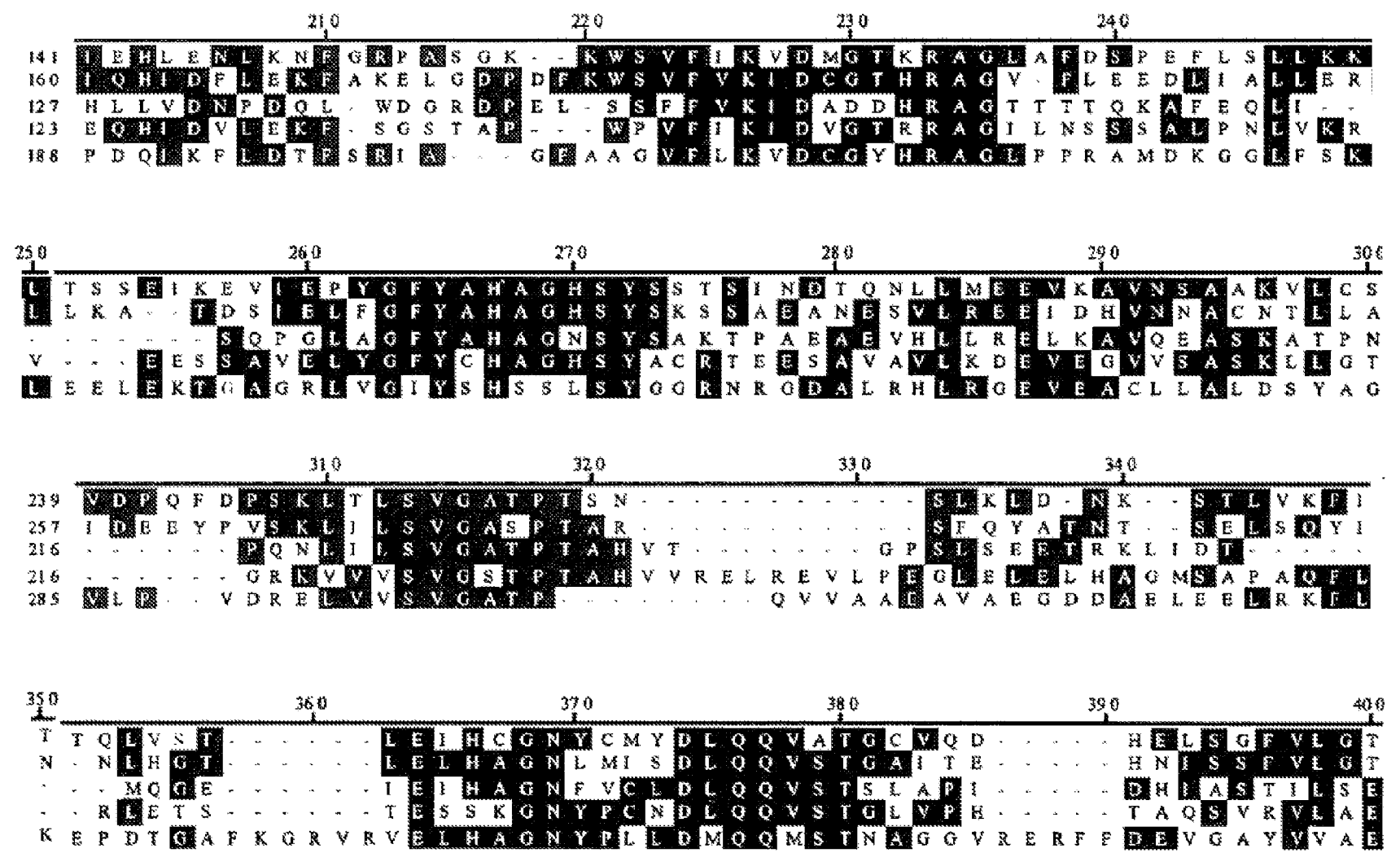

Next, in order to clarify a structural characteristic of the novel enzyme, we searched database for a protein having a sequence homologous to an amino acid sequence of the novel enzyme. As a result, as shown in FIG. 3, it is determined that any of proteins having sequences homologous to the amino acid sequence of the novel enzyme are proteins with unknown function and that the novel enzyme does not have a homology to the already-known D-serine dehydratase in primary structure.

(5) Investigation of Substrate-Specificity

The substrate-specificity of the novel enzyme was examined by the following method. That is to say, as the substrate, L-serine and D-threonine in addition to D-serine were prepared, and the reactivity of the enzyme with respect to each substrate was examined by the Nessler method. Note here that the reactivity of the enzyme with respect to L-serine or D-threonine was examined by the Nessler method in the same conditions as in the case of D-Serine except that L-serine (Wako Pure Chemical Industries, Ltd.) or D-threonine (Wako Pure Chemical Industries, Ltd.) was used as a substrate.

Figures 4, 5:
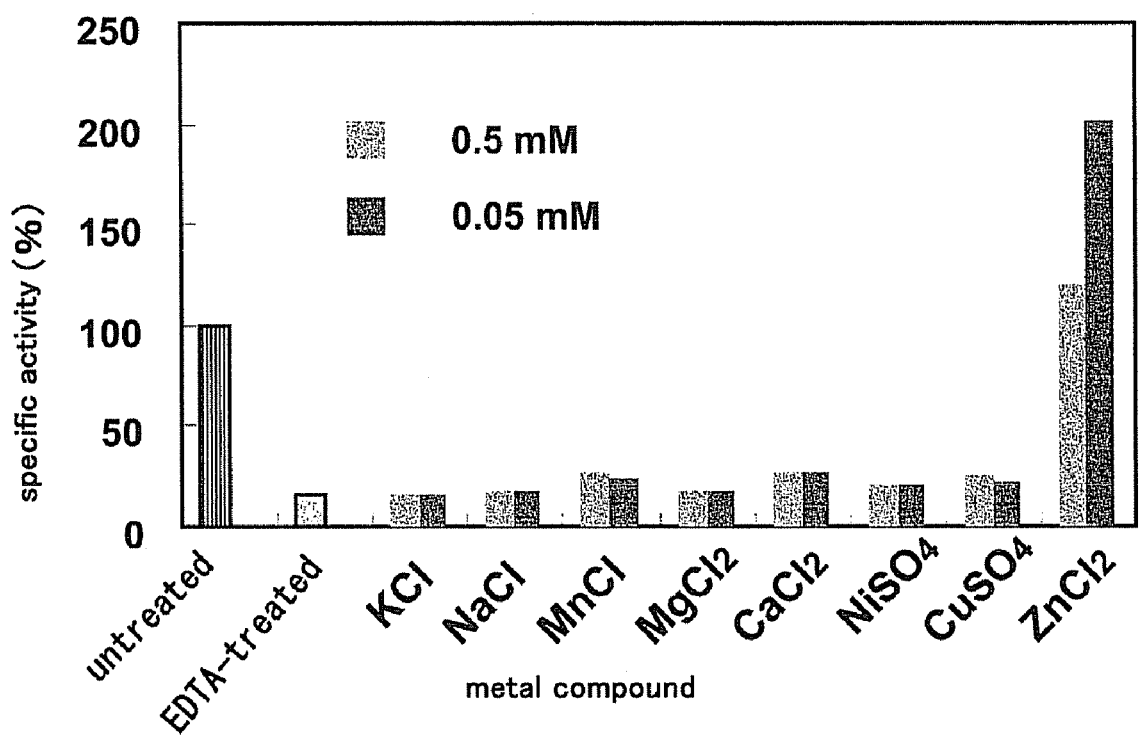
FIG. 4 is a table showing a substrate-specificity of the novel D-serine dehydratase. The substrate-specificity of the novel D-serine dehydratase and the substrate-specificity of the already-known enzyme (*Escherichia coli* D-serine dehydratase) are compared with each other. The novel D-serine dehydratase does not react with L-serine at all and the reactivity with respect to D-threonine is extremely low.
FIG. 5 is a graph showing an influence of a metal ion on the enzymatic activity of the novel D-serine dehydratase. The novel D-serine dehydratase is inhibited by EDTA and activated by a low-concentration zinc ion.

The results are shown in FIG. 4. As is apparent from FIG. 4, the novel enzyme (left) shows no reactivity with respect to L-serine and low reaction with respect to D-threonine. Thus, it has been clarified that the novel enzyme has an extremely excellent substrate-specificity with respect to D-serine.

(6) Influence of metal ion on enzymatic activity

The influence and effect of metal ion on the activity of the novel enzyme were examined by the following method. The compounds shown in FIG. 5 were incubated with untreated novel enzyme and 2 mM EDTA, and then dialyzed with Tris buffer solution. The D-serine dehydratase activity of the novel enzyme was measured by a Nessler method in the presence of 0.05 mM or 0.5 mM of any of KCl, NaCl, $MnCl_2$, $MgCl_2$, $CaCl_2$, $NiSO_4$, $CuSO_4$ and $ZnCl_2$.

The results are shown in FIG. 5. As is apparent from FIG. 5, it has been clarified that the novel enzyme is mostly deactivated by EDTA treatment and that it is activated by the addition of zinc. Furthermore, when the same experiment was carried out while changing the zinc concentration, it has been determined that when the zinc concentration was 0.005 mM, the enzymatic activity was increased most.

(7) Effect of pH on Enzymatic Activity

The relationship between the activity of the novel enzyme and pH at the reaction was examined by the following method. In the Nessler method, buffer solution was changed to MOPS (pH 6.5-8.0), MES (pH 6.0-6.5), HEPES (pH 7.0-8.5), and Tris (pH 7.5-9.0), respectively. By using the reaction solution, the D-serine dehydratase activity of the novel enzyme was measured.

Figure 6:
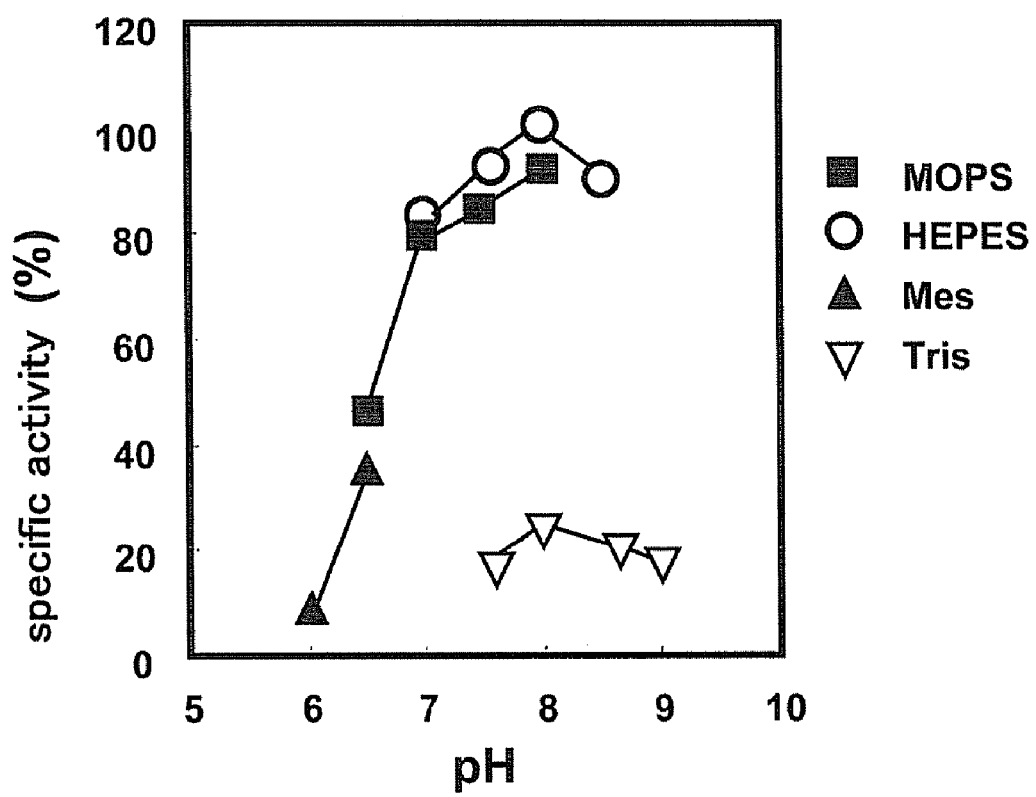
FIG. 6 is a graph showing an effect of pH on the enzymatic activity of the novel D-serine dehydratase. The novel enzyme shows a high activity when MOPS and HEPES buffer are used. Optimum pH is around 8 and an excellent reactivity is observed in the pH ranging from about 7.5 to about 9.0.

The results are shown in FIG. 6. As is apparent from FIG. 6, the optimum pH of the novel enzyme is around 8 and an excellent reactivity is observed when the pH is in the range from about 7.5 to about 9.0.

(8) Investigation of Dynamic Characteristic

The dynamic characteristic of the novel enzyme was examined by the following method. In the Nessler method, the concentration of D-serine was changed and the D-serine dehydratase activity of the novel enzyme in the respective concentrations of D-serine was measured. The inverse number of the obtained rate was plotted to the inverse number of the D-serine concentration. Then, the maximum rate was calculated from the inverse number of the y section and Km value was calculated from the inverse number of the x section.

Figures 7, 8:
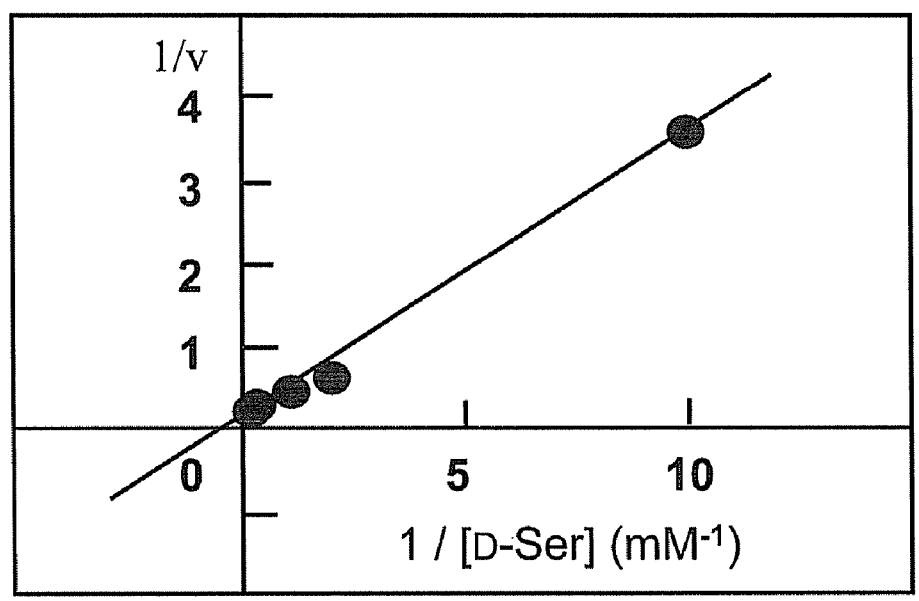
FIG. 7 is a graph showing a dynamic characteristic of the novel D-serine dehydratase. From the reciprocal plot of a reaction rate with respect to the reciprocal of the concentration of D-serine, Vmax value of the novel D-serine dehydratase is calculated to 4.2 mmol/min/mg and a Km value with respect to D-serine is calculated to 0.46 mM.
FIG. 8 shows a comparison between a quantification method (enzyme method) using the novel D-serine dehydratase and a conventional method. The concentration of D-serine in human urine is quantified by an enzyme method and a conventional method, respectively, and the results are compared with each other.

The results are shown in FIG. 7. As is apparent from FIG. 7, the maximum rate was 4.2 μmol/min/mg and the Km value was calculated to be 0.46 mM.

3. Quantification Method of D-Serine (1) Quantification of D-Serine

The serum (50 μl) is prepared from the peripheral blood of the subject (serum sample). The serum sample is diluted 10 times with 10 mM HEPES-NaOH buffer (pH 8.0), and then, 10 μl of 2 μM pyridoxal-5'-phosphate solution and 1 nmol D-serine dehydratase are added. Then, the mixture is incubated at 30° C. for 10 minutes. Thereafter, trichloroacetic acid (final concentration: 5%) is added so as to stop the reaction. After centrifugation (10,000 rpm for 5 minutes), ammonia contained in the supernatant is quantified by the use of a Nessler reagent.

The above-mentioned quantification method is carried out by using a standard reagent containing a predetermined amount of D-serine (1 mM, 10 mM, 50 mM and 100 mM) instead of the serum sample, and a calibration curve showing the relationship between the quantified value of ammonia and the D-serine content is formed. Based on this calibration curve, from the quantified value of ammonia obtained with respect to the serum sample, the amount of D-serine in the serum sample is calculated.

(2) Measurement of Ratio of Amount of D-Serine to Total Amount of Serine (2-1) Quantification of Amount of D-Serine The serum (50 μl×2) is prepared from the peripheral blood of the subject (serum samples 1 and 2). D-serine in the serum sample 1 is quantified by the same procedure as in (1).

(2-2) Quantification of Total Amount of D-Serine

On the other hand, total serine in the serum sample 2 is quantified by the following method. The serum sample 2 is diluted 10 times with 10 mM HEPES-NaOH buffer (pH 8.0), 10 μl of 2 μM pyridoxal-5'-phosphate solution, 1 nmol serine racemase, and 1 nmol D-serine dehydratase are added, and incubated at 30° C. for 10 minutes. Thereafter, trichloroacetic acid (final concentration: 5%) is added so as to stop the reaction. After centrifugation (10,000 rpm for 5 minutes), ammonia contained in the supernatant is quantified by the use of Nessler reagent. Based on a calibration curve formed by the same method as in (1), the amount of D-serine in the serum sample 2 is calculated from the quantified value of ammonia. Herein, the principle of the quantification method is mentioned below. With the action of serine racemase, L-serine in the serum sample is converted into D-serine. Thus generated D-serine and the originally existing D-serine are quantified by D-serine dehydratase.

Note here that serine racemase of *Dictyostelium discoideum* that is thought to be most suitable for this measurement method from the activity and stability can be prepared by the following method. A serine racemase gene (DDB0230209) of *D. discoideum* is amplified by PCR using Dicty cDB clone as a template and a primer designed to have six His residues at C-terminal. *Escherichia coil* Rosetta strain is transformed by using an expression vector constructed by inserting the obtained DNA fragment into pET16b (Novagen), and IPTG is added so as to express serine racemase. Purification of serine racemase is carried out by the use of Ni—NTA-Bind Resins (Novagen). An example of the serine racemase used in the measurement may include an enzyme derived from bacteria (as to the preparation method, see, for example, Arias C. A. et al., (2000) Microbiology 146, 1727-1734), and alanine racemase derived from bacteria which catalyze the racemization of serine as a side reaction (as to the preparation method, see, Tanizawa K. et al. (1988), Biochemistry. 27, 1311-1316), and low substrate-specificity amino acid racemase (as to the preparation method, see, Lim Y H, et al. (1993) J Bacteriol. 175, 4213-4217) in addition to the enzyme derived from *Dictyostelium discoideum*.

From the results of (2-1) and (2-2), the ratio of the amount of D-serine to the total amount of serine of serine (D-serine amount/total amount of serine) is calculated.

4. Human Urinary D-Serine Quantification (1) Method

A reaction solution (200 μl) containing various amounts of human urine (stored at −20° C.), 50 mM HEPES-NaOH buffer solution (pH 8.0), 20 μM PLP, 0.3 mM NADH, 2 units of lactate dehydrogenase derived from rabbit muscle and 2 μg of D-serine dehydratase (novel enzyme prepared in 2) was incubated at 37° C. for 30 minutes, and the decrease in absorbance at 340 nm, which is derived from NADH, was measured.

Furthermore, as a control, by a conventional method of separating-quantifying fluorescence diastereomerized D-serine by HPLC, D-serine of the same sample was quantified.

(2) Results

The concentration of D-serine in urine quantified by the present enzyme method was 243±7.0 μM (mean value±standard deviation) (n=6, CV 2.9%) (FIG. 8). Meanwhile, the concentration of D-serine quantified by the HPLC method was 239±9.8 μM (mean value±standard deviation) (n=6), showing good conformity.

Figure 9:
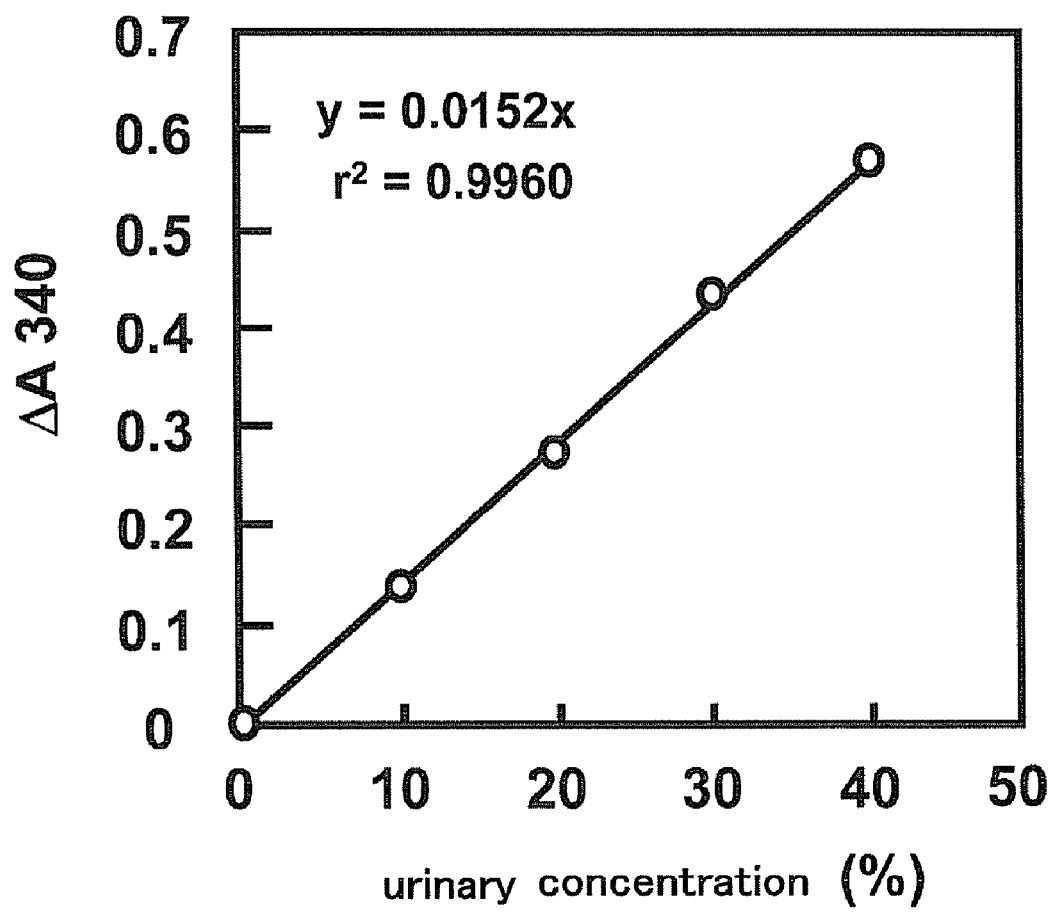
FIG. 9 is a graph showing a relationship between the urinary concentration and the decrease in absorbance at 340 nm when the measuring is carried out by an enzyme method.

When the decrease in absorbance at 340 nm with respect to the urinary concentration at the time of measurement was plotted, good linearity with $r^2$=0.996 was obtained (FIG. 9).

This suggests that urine components other than D-serine do not affect the present enzyme quantification method.

INDUSTRIAL APPLICABILITY

A novel D-serine dehydratase disclosed in this specification has a high substrate-specificity with respect to D-serine. With a quantification method of the present invention using such an enzyme having an excellent substrate-specificity, even if a sample includes a contaminated material (in particular, L-serine), it is possible to accurately quantify D-serine. Therefore, the quantification method of the present invention is a suitable method for quantifying D-serine in a living body sample. Furthermore, the quantification method of the present invention enables D-serine in a living body sample whose L-serine content is much larger than D-serine content to be quantified under the condition where quantification is not possible with a conventional enzyme. Thus, the quantification method of the present invention is expected to be applied to diagnosis of human or mammalian nervous diseases such as schizophrenic disorder and Alzheimer's disease or BSE (Bovine Spongiform Encephalopathy), On the other hand, the quantification method of the present invention can be carried out by using extremely a general microplate reader and a spectrophotometer. The quantification method of the present invention has also large advantages: complicated pre-treatment is not required; and a kit for carrying out this method can be easily produced. Furthermore, the quantification method of the present invention can be carried out by a simple and easy operation and does not require skill for analyzing data. Furthermore, this method can be carried out by using a disposable instrument such as microplate, which contributes to the reduction of risk of infection to workers handling living body samples. In addition, according to the quantification method of the present invention, economical cost and time cost, which were problems in a conventional quantification method of D-serine, can be radically reduced. Thus, this method is expected to be applied to mass health examination, and the like.

The present invention is not limited to the description of the above exemplary embodiments and Examples. A variety of modifications, which are within the scopes of the following claims and which are easily achieved by a person skilled in the art, are included in the present invention.

Contents of the theses, Publication of Patent Applications, Patent Publications, and other published documents referred to in this specification are herein incorporated by reference in its entity.

The invention claimed is:

1. A D-serine quantification method comprising the following steps of:
   (1) preparing a reagent;
   (2) adding a D-serine dehydratase into the sample and reacting with each other, wherein the D-serine dehydratase comprises the following protein (a) or (b):
   (a) a protein having the amino acid sequence set forth in SEQ ID NO: 1; or
   (b) a protein having 95% or more identity with the amino acid sequence set forth in SEQ ID NO: 1 and having a D-serine dehydratase activity;
   (3) quantifying ammonia or pyruvic acid generated as a result of (2); and (4) calculating an amount of D-serine in the sample from the quantified value obtained in (3).

2. The D-serine quantification method according to claim 1, the method further comprising the following steps of:
 (5) adding amino acid racemase to a reaction solution after the step (2) and reacting with each other in a coexistence of the D-serine dehydratase;
 (6) quantifying ammonia or pyruvic acid generated as a result of (5); and
 (7) calculating a total amount of serine in the sample from the quantified value obtained in (6) and the amount of D-serine calculated in (4).

3. A D-serine quantification method including the following steps of:
 (1) preparing a sample:
 (2) adding a D-serine dehydratase to a part of the sample so as to react with each other, wherein the D-serine dehydratase comprises the following protein (a) or (b):
 (a) a protein having an amino acid sequence set forth in SEQ ID NO: 1; or
 (b) a protein having 95% or more identity with the amino acid sequence set forth in SEQ ID NO: 1 and having a D-serine dehydratase activity;
 (3) quantifying ammonia or pyruvic acid generated as a result of (2); and
 (4) calculating an amount of serine in the sample from the quantified value obtained in (3);
 (5) adding a D-serine dehydratase and amino acid racemase to another part of the sample and reacting with each other, wherein the D-serine dehydratase comprises the following protein (a) or (b):
 (a) a protein having an amino acid sequence set forth in SEQ ID NO: 1; or
 (b) a protein having 95% or more identity with the amino acid sequence set forth in SEQ ID NO: 1 and having a D-serine dehydratase activity;
 (6) quantifying ammonia or pyruvic acid generated as a result of (5); and
 (7) calculating a total amount of serine in the sample from the quantified value obtained in (6).

4. The D-serine quantification method according to claim 1, wherein the D-serine dehydratase does not react with L-serine.

5. The D-serine quantification method according to claim 1, wherein a reactivity of the D-serine dehydratase to D-threonine is not more than 5% when a reactivity of the D-serine dehydratase to D-serine is 100%.

6. The D-serine quantification method according to claim 1, wherein the D-serine dehydratase is a recombinant protein expressed in *Escherichia coli* as a host.

* * * * *

SEQUENCE LISTING

<160> NUMBER OF SEQ ID NOS: 4

<210> SEQ ID NO 1
<211> LENGTH: 428
<212> TYPE: PRT
<213> ORGANISM: Saccharomyces cerevisiae

<400> SEQUENCE: 1

```
Met Ser Asp Val Leu Ser Gln Tyr Lys Gly Cys Ser Val Arg Asp Leu
1               5                   10                  15

Pro Thr Pro Asn Phe Val Ile Asn Glu Glu Lys Phe Asp Lys Asn Cys
            20                  25                  30

Thr Thr Met Leu Asn Asn Val Glu Lys Leu Ser Gln Glu Cys Gly Val
        35                  40                  45
```

Pro Ile Lys Phe Arg Ala His Val Lys Thr His Lys Thr Ala Lys Gly
        50                  55                  60

Thr Leu Lys Gln Leu Gly His Gly Leu Pro Leu Ala Lys Arg Thr Thr
65                  70                  75                  80

Arg Ala Ile Leu Val Ser Thr Leu Lys Glu Ala Glu Leu Leu Asn
                85                  90                  95

Tyr Gln Asp Arg Gln Cys Ser Asp Tyr Ile Asp Asp Ile Thr Tyr Ser
                100                 105                 110

Leu Pro Cys Cys Val Pro Glu Phe Ile Pro Leu Leu Ser Asn Leu Ser
                115                 120                 125

Arg Arg Val Asn Asn Phe Gln Val Phe Val Asp Asn Ile Glu His Leu
        130                 135                 140

Glu Asn Leu Lys Asn Phe Gly Arg Pro Ala Ser Gly Lys Lys Trp Ser
145                 150                 155                 160

Val Phe Ile Lys Val Asp Met Gly Thr Lys Arg Ala Gly Leu Ala Phe
                165                 170                 175

Asp Ser Pro Glu Phe Leu Ser Leu Leu Lys Lys Leu Thr Ser Ser Glu
                180                 185                 190

Ile Lys Glu Val Ile Glu Pro Tyr Gly Phe Tyr Ala His Ala Gly His
        195                 200                 205

Ser Tyr Ser Ser Thr Ser Ile Asn Asp Thr Gln Asn Leu Leu Met Glu
210                 215                 220

Glu Val Lys Ala Val Asn Ser Ala Ala Lys Val Leu Cys Ser Val Asp
225                 230                 235                 240

Pro Gln Phe Asp Pro Ser Lys Leu Thr Leu Ser Val Gly Ala Thr Pro
                245                 250                 255

Thr Ser Asn Ser Leu Lys Leu Asp Asn Lys Ser Thr Leu Val Lys Phe
                260                 265                 270

Ile Thr Thr Gln Leu Val Ser Thr Leu Glu Ile His Cys Gly Asn Tyr
        275                 280                 285

Cys Met Tyr Asp Leu Gln Gln Val Ala Thr Gly Cys Val Gln Asp His
        290                 295                 300

Glu Leu Ser Gly Phe Val Leu Gly Thr Val Leu Ser Ser Tyr Pro Ser
305                 310                 315                 320

Arg Gly Glu Leu Leu Ser Asn Thr Gly Val Met Cys Leu Thr Arg Glu
                325                 330                 335

Ala Ser Ser Ile Lys Gly Phe Gly Ile Cys Ala Asp Leu Glu His Val
                340                 345                 350

Leu Lys Ser Glu Ser Phe Ser Arg Glu Trp Tyr Val Ala Arg Val Ser
        355                 360                 365

Gln Glu His Gly Ile Leu Arg Pro Ile Arg Asn Trp Asn Glu Thr Thr
370                 375                 380

Pro Leu Lys Leu Gly Ser Lys Ile Ala Val Leu Pro Gln His Ala Cys
385                 390                 395                 400

Ile Thr Met Gly Gln Phe Pro Tyr Tyr Phe Val Val Asn Ser Glu Gly
                405                 410                 415

Ile Val Asn Asp Val Trp Leu Pro Phe Gln Lys Trp
                420                 425

<210> SEQ ID NO 2
<211> LENGTH: 1287
<212> TYPE: DNA
<213> ORGANISM: Saccharomyces cerevisiae

<400> SEQUENCE: 2

-continued

```
atgagcgatg ttctatctca atataaaggg tgctcagtca gagatttacc cacacccaat      60
ttcgttatta atgaagaaaa atttgataag aattgtacga caatgttgaa caacgttgaa     120
aagctcagcc aggaatgtgg cgtaccaatc aaatttcgtg cacacgtaaa aacgcataag     180
acagcaaagg gaactttgaa acaattgggc cacggacttc cattggctaa acgcactaca     240
agagccatat tagtatcaac tttgaaagaa gcagaagaac ttcttaatta tcaagataga     300
caatgttcgg attatattga cgatataaca tatagtttac cctgttgcgt tccagagttt     360
attcctcttt tgagcaattt gtcaagaagg gtgaataatt ttcaggtttt tgttgataac     420
attgaacact tggagaattt aaagaatttc ggtaggcctg cttccggcaa gaaatggtcg     480
gtttttatca aggttgatat ggggactaag agggcaggtc ttgctttcga ctctccagaa     540
tttttgagtc tttaaaaaa actgacttcc tcagaaatta aagaagtaat tgagccatat     600
gggttttatg ctcatgccgg acacagctac tcttcaacct cgatcaacga cactcagaat     660
cttttgatgg aagaagtgaa agcagtcaat tctgccgcta aagttttgtg ctctgtggat     720
cctcagtttg atccttctaa attaacactt tctgtgggcg ctactccgac ttccaattct     780
ttgaaactcg ataataaaag taccttgtt aaattcatta ctactcaatt agttagtacg     840
cttgaaatcc actgcggtaa ttactgcatg tatgacctgc aacaggtggc aacaggctgt     900
gtccaagatc acgaattgtc tggttttgta ttaggaacag tactatcatc ttacccttct     960
agaggtgaat tgttgagtaa tacaggtgta atgtgtctaa cgcgagaagc atcctcaata    1020
aaagggtttg gaatatgtgc tgatttggaa catgtgttaa aatccgagag tttcagtagg    1080
gaatggtatg tagcaagggt ctctcaagaa cacgggatac tgaggccaat aagaaactgg    1140
aacgaaacta ctccattaaa attaggcagc aaaattgccg tccttcctca acacgcttgt    1200
atcacaatgg gacaatttcc atattatttc gtggtaaaca gcgaaggcat tgtcaacgat    1260
gtttggttac cttttcagaa atggtaa                                        1287
```

<210> SEQ ID NO 3
<211> LENGTH: 37
<212> TYPE: DNA
<213> ORGANISM: Artificial
<220> FEATURE:
<223> OTHER INFORMATION: PCR primer

<400> SEQUENCE: 3

```
atgctcgagg ttctatctca atataaaggg tgctcag                              37
```

<210> SEQ ID NO 4
<211> LENGTH: 38
<212> TYPE: DNA
<213> ORGANISM: Artificial
<220> FEATURE:
<223> OTHER INFORMATION: PCR primer

<400> SEQUENCE: 4

```
accaagctta ccatttctga aaaggtaacc aaacatcg                             38
```